United States Patent [19]

Wellisz

[11] Patent Number: 5,433,748
[45] Date of Patent: Jul. 18, 1995

[54] AURICULAR IMPLANT
[75] Inventor: Tadeusz Wellisz, Los Angeles, Calif.
[73] Assignee: Porex Technologies Corp., Fairburn, Ga.
[21] Appl. No.: 800,522
[22] Filed: Dec. 4, 1991
[51] Int. Cl.$^6$ .................................................. A61F 2/18
[52] U.S. Cl. .................................................. 623/10
[58] Field of Search .................. 623/10, 16, 11, 12

[56] References Cited

U.S. PATENT DOCUMENTS

| 3,257,668 | 6/1966 | Braley. |  |
|---|---|---|---|
| 3,681,786 | 8/1972 | Lynch. |  |
| 4,306,318 | 12/1981 | Mano et al. | 623/12 |
| 4,595,713 | 6/1986 | St. John. |  |
| 4,813,958 | 3/1989 | Dixon | 623/13 |
| 4,832,681 | 5/1989 | Lenck | 623/12 |
| 5,041,138 | 8/1991 | Vacanti et al. |  |
| 5,053,049 | 10/1991 | Campbell. |  |
| 5,078,743 | 1/1992 | Mikalov et al. | 623/11 |
| 5,108,407 | 4/1992 | Geremia et al. | 623/12 |

FOREIGN PATENT DOCUMENTS

| 0002068 | 5/1979 | European Pat. Off. | 623/10 |
|---|---|---|---|
| 683737 | 7/1979 | U.S.S.R. | 623/10 |

OTHER PUBLICATIONS

"Review of Current Status of Cochlear Prosthesis", White, Apr., 1982, Transactions on Biomedical Engineering, pp. 233-238.

Berghaus, Alexander; "Porecon Implant and fan Flap: A Concept for Reconstruction of the Auricle"; pp. 451-457; Facial Plastic Surgery, vol. 5, No. 5, Oct. 1988.

Brent, Burt et al. "Secondary Ear Reconstruction with Cartilage Grafts Covered by Axial, Random, and Free Flaps of Temporoparietal Fascia" pp. 141-151. Plastic and Reconstructive Surgery, vol. 72, No. 2, Aug. 1983.

Primary Examiner—David Isabella
Attorney, Agent, or Firm—Lane, Aitken & McCann

[57] ABSTRACT

An auricular implant includes a strip of flexible material having pores into which tissue can grow. The strip has the shape of a helix, the strip having an inner end adjacent to the center of the helix, an outer end at the periphery of the helix, an outer surface convex in a transverse direction, and an inner surface concave in a transverse direction. The material has the capability of attaching itself to tissue, the flexible strip being attached to the head of a patient at the inner and outer ends and unattached to the head between the inner and outer ends. A base member simulating the antihelix of an auricle has a flat bottom surface and a peaked upper portion.

17 Claims, 3 Drawing Sheets

FIG. 3A
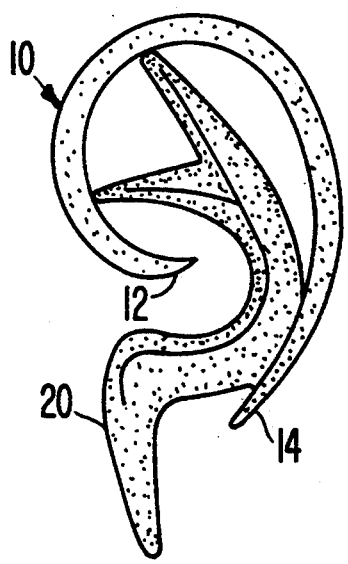
FIG. 3B
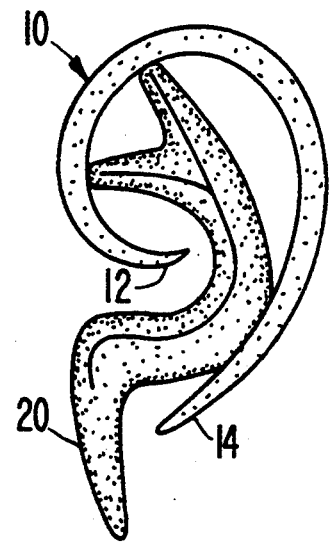
FIG. 3C
FIG. 3D
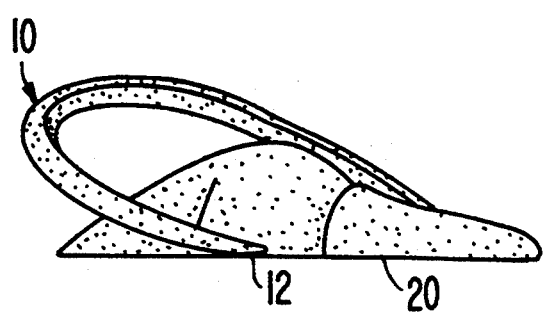
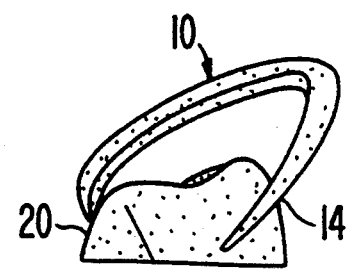
FIG. 4A
FIG. 4B
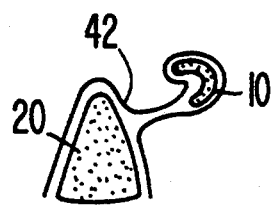
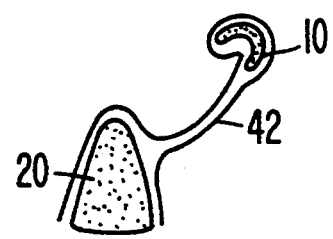

AURICULAR IMPLANT

BACKGROUND OF THE INVENTION

The present invention relates to an implant used to create or reconstruct the human auricle (external ear).

The incidence of people born with an absence or severe deformity of the auricle is 1:7,000. There are also a large number of traumatic injuries to the ear, especially in cases of severe facial burns.

Known implants to remedy these problems fall into two general categories. In the first category are preformed, single piece implants simulating the entire ear. In the second category are implants that are created on a custom basis, either prior to or at the time of surgical implantation. The disadvantages of the known constructions include their inability to fold in on themselves. In addition, pre-formed implants simulating the entire ear are not amenable to significant subsequent alterations of their shape. Furthermore, known one-piece designs cannot achieve sufficient detail.

SUMMARY OF THE INVENTION

The implant according to the present invention comprises a strip of porous material which permits the ingrowth of tissue and which, when covered with soft tissue, can create an ear of almost any size or shape. A first object of this invention is to have an implant that can be pre-formed and can be used in any person with only minor modifications. The implant allows for a sturdy, non-rigid construction that results in a detailed, high profile ear reconstruction, that is, a reconstruction in which the ear projects from the side of the head, with a space between projecting portions and the head, as in a natural ear. A second object is to have a high profile design that can fold down upon itself when external pressure is applied to minimize injury to the patient and the implant.

The implant according to the present invention is constructed using a bioimplantable material, especially, porous high density polyethylene. With such a porous material, tissue grows into the implant and forms a highly vascularized integrated structure. Through the action of the tissue, implants which are cut or nicked or otherwise damaged repair themselves because tissue grows into the damaged areas.

The implants can either be hand carved or manufactured. The porous high density polyethylene implant material can be manufactured in the form of a long strip which a surgeon can cut to a desired length and formed to a desired shape, called the helix, representing the coiled helical rim of the auricle. The ends of the helix are cut and tailored to a given size depending on the length and tightness of the curve that is required for the given reconstruction. The helix is attached at its ends to the side of the head and spaced between its ends from the head and from inner portions of the ear. Soft tissue to fill the space between the helix and inner portions of the ear is provided by known methods of providing soft tissue coverage. Projection of the helix in relation to the base block is easily determined by adjusting the angle of the helix in relation to the side of the head so that either a low or high projection can be achieved.

Projecting portions of the implant can fold on themselves in the event that pressure is applied to the helix to minimize trauma to the helical rim, such as that incurred when the side of the head is struck. The helix can also pivot relative to its attached ends similar to the handle of a bucket.

A second component, called a base block and made of the same material as the helix, represents the anatomical structures of the auricle excluding the helical rim. Base blocks used for the right and left ear are mirror images of each other. The base block is useful in cases where there is complete absence of an ear. It simulates the valleys and folds of the inner portion of the ear, and the simulation becomes more realistic when the base block is covered with soft tissue. The base block can also be easily modified as needed to create ears of different sizes and shapes. Improved detail can be achieved using the two-piece design when the inner portion of the auricle is missing from the patient.

The advantages of the present invention include: an auricle of almost any size or shape can be created using the implant; the construction allows the implant to fold in on itself in the event that external pressure is applied to the implant; and more detail can be achieved creating a more realistic external ear reconstruction. A preformed implant can be used to reconstruct variously shaped ears with greater ease of use, improved aesthetic results and the ability of the implant to fold in on itself.

BRIEF DESCRIPTION OF THE DRAWINGS

FIG. 3A is a top view of one form of the two-piece implant according to the present invention;

FIG. 3B is a second form of the two-piece implant according to the present invention;

FIG. 3C is a left elevation of the implant of FIG. 3A;

FIG. 3D is an inferior elevation of the implant of FIG. 3A;

FIG. 4A is a schematic cross section of the two-piece implant with soft tissue covering the implant;

FIG. 4B is a schematic cross section of another form of the implant according to the present invention;

DETAILED DESCRIPTION OF THE PREFERRED EMBODIMENTS

Figure 1A:
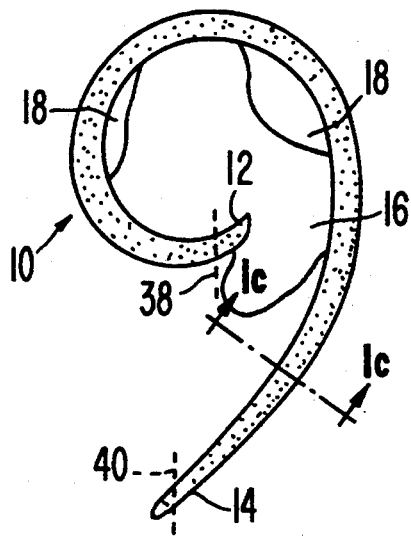
FIG. 1A is a top view of a helix, used for the left ear, of the two-piece auricular implant according to the present invention.
Figure 1B:
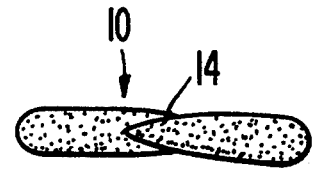
FIG. 1B is an inferior elevation of the helix of FIG. 1A.
Figure 1C:
FIG. 1C is a cross section taken along the line 1C—1C in FIG. 1A.

As can be seen from FIGS. 1A–1C, the implant according to the present invention comprises a generally helical strip or helix 10 of porous material which permits the ingrowth of tissue and which defines a frame for a covering of tissue. The helix 10 has an inner end 12, near the center of the helix, and an outer end 14 at the periphery of the helix.

The helix 10 is constructed using a bioimplantable material, especially, porous high density polyethylene. With such a porous material, tissue grows into the tissue and forms a highly vascularized integrated structure. Through the action of the tissue, implants which are cut or nicked or otherwise damaged repair themselves because tissue grows into the damaged areas. The helix 10 can either be hand carved or manufactured. The porous, high density, polyethylene implant material can be manufactured in the form of a long strip which a surgeon can cut to a desired length and form to a desired shape, the helix 10, representing the coiled helical rim of the auricle. The ends of the helix 10 are cut and tailored to a given size depending on the length and tightness of the curve that is required for the given reconstruction. The helix 10 is attached at its ends to the side of the head and spaced between its ends from the head and from inner portions of the ear. Soft tissue to fill the space between the helix 10 and inner portions of the ear is provided by known methods of providing soft tissue coverage. Projection of the helix 10 in relation to the side of the head is easily determined by adjusting the angle of the helix 10 in relation to the side of the head so that either a low or high projection can be achieved.

As can be seen from FIG. 1A, the helix 10 is positioned in the appropriate site on the side of the head of the patient adjacent to any auricle portion which the patient has, such as the portion 16 of, for example, a burn patient. The helix 10 may contact some points on the ear portion 16 and define spaces 18 with the ear portion 16 along other parts of the helix 10. When a soft tissue covering is provided over the helix 10, with the helix 10 acting as a frame, the spaces 18 are covered, as in the helix itself.

As can be seen from FIG. 1C, the helix can also be any curvilinear shape that represents the helical rim and earlobe. On cross section, the helical rim can be a rim of any shape or thickness including a crescent, a "c", or a half circle. The material for the helix can be manufactured as an elongate strip having a constant cross section of the types of curvatures just described. Typically, the strip has a thickness of 1.5 mm and the external diameter of its curved cross-section is 6–8 mm. The surgeon can cut the strip to the desired length, shape it in curvature lengthwise to define the desired curvature of the rim of the ear and adjust the curvature in cross section. In addition, the helix can be cut or shaved using a scissors or a knife.

The helix 10 is constructed from a biomaterial that is somewhat flexible and can be hand carved by the surgeon in the operating room to allow for the necessary modifications to customize the implant for each individual patient. A porous material that is stable and allows for tissue ingrowth is preferable. A material which has worked well is a highly porous high density polyethylene which is commercially available under the name MEDPOR ® Surgical Implant, from Porex Technologies Corp. of Fairburn, Ga. This material is extremely strong, completely inert, durable and flexible over time. It has a contiguous large pore structure which allows blood to flow through. It is rapidly vascularized with soft tissue ingrowth and collagen deposition in the pores. It is strong enough to resist the deformation of its pores and to support eyeglasses. Implants of this material appear to be highly resistant to infection.

Surgical implantation involves creating a subcutaneous pocket in the appropriate location. One end of the helix is inserted into the pocket. The end of the helix can be cut or shaven, if necessary, using a scissors or knife, to fit into the pocket. It has been found that the porous, high density, polyethylene material of the implant attaches securely on its own to the tissue around the pocket in a manner similar to that of a VELCRO ® fastener. There is usually no need to suture the end of the helix in place.

Soft tissue must cover the implant entirely. This soft tissue coverage can be achieved in any of the following three conventional ways for obtaining soft tissue coverage: 1) the skin of the area can be undermined, and because of its inherent elasticity, can be used to cover the implant; 2) the soft tissue can be pre-expanded to achieve adequate coverage; and 3) a flap of adjacent tissue, such as the temporoparietal fascial flap with a split thickness skin graft, can be used. Subsequent surgical revisions will be required, such as a post auricular skin graft to adjust the final projection of the helix of the two-piece implant.

Alternate methods of construction include fabricating the implant using any bioimplantable material. These include any form of a bone or bone substitute, any form of cartilage, either solid or porous plastic, synthetic mesh, silicone, metal, ceramic, and hydroxyapatite.

A second component, called a base block 20, which represents the anatomical structures of the auricle excluding the helical rim can be made of the same material as the helix 10. Base blocks used for the right and left ear are mirror images of each other. The base block 20 is useful in cases where there is complete absence of an ear. It simulates the valleys and folds of the inner portion of the ear, and the simulation becomes more realistic when the base plate 20 is covered with soft tissue. The base block 20 can also be easily modified as needed to create ears of different sizes and shapes.

Figure 2A:
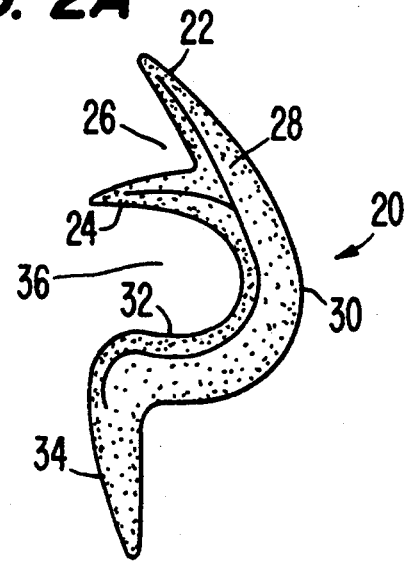
FIG. 2A is a top view of a base block for the left ear of the two-piece auricular implant according to the present invention.
Figure 2B:
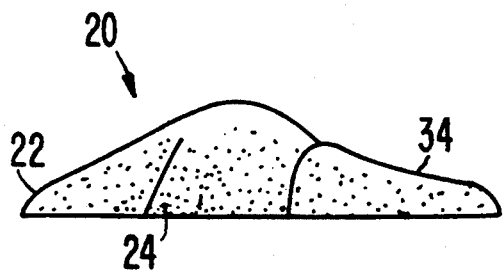
FIG. 2B is a left elevation of the base block of FIG. 2A.
Figure 2C:
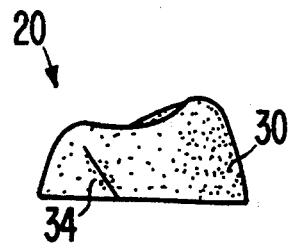
FIG. 2C is an inferior elevation of the base block of FIG. 2A.

The base block 20 can be of any form that is a representation of a part or the entire auricle. As can be seen from FIG. 2A, the base block 20 simulates the folds and valleys of the inner portion of the ear including the superior crus 22 and inferior crus 24 defining the fossa triangularis 26 and merging into the antihelix 28. Below the antihelix 28 is the helix 30 of the inner portion of the ear, which is not to be confused with the helix 10 defining the coiled helical rim of the ear. The helix 30 extends into a forward bend 32 in the base member 20 which simulates the antetragus, from which a lobule 34 depends. The space defined between the inferior crus 24 and the antetragus is the concha 36 into which the ear canal opens. When the base block 20 is covered with soft tissue, it more closely resembles the folds and valleys of the inner portion of the ear. The folds and valleys are accentuated in the base block 20, and the accentuation is reduced in the covering of soft tissue. The soft tissue covering is considerably thicker than the very thin tissue covering the inner portions of a natural ear, which thin tissue has not yet been capable of duplication in covering an implant.

FIGS. 3A–3D illustrate typical relative positions of the helix 10 relative to the base block 20. As can be seen, the helix of the implant of FIG. 3B is tighter than the helix of the implant of FIG. 3A.

As can be seen from FIGS. 4A and 4B, which are schematic cross-sections through an implant including a helix 10 and a base block 20, the helix can be positioned close to the base block and have a low projection angle relative to the side of the head, which would lie in a generally horizontal plane as viewed in these figures. Alternatively, the helix 10 can be well spaced from the base block 20 and lie at a high projection angle relative to the side of the head. It will be apparent that a very large variety of other relative orientations of the helix and base block between and beyond the orientations shown in FIGS. 4A and 4B are possible. Soft tissue 42 covers the helix 10 and the base block 20 and connects them to one another.

Figure 4C:
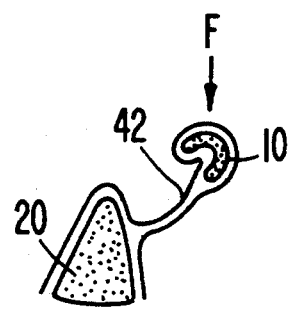
FIG. 4C is a schematic cross section of another form of the implant according to the present invention prior to the application of external pressure.

FIG. 4C shows a schematic cross-section through an implant according to the present invention prior to the application of a force represented by the arrow F.

Figure 4D:
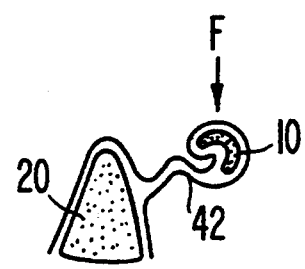
FIG. 4D is a schematic cross section of the implant of FIG. 4C after the application of external pressure.
Figure 5A:
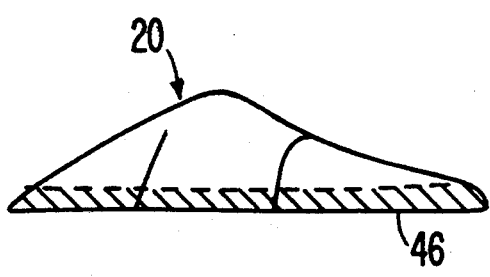
FIG. 5A is a left elevation of a base block for use as the left ear showing an exemplary shaded portion which can be removed to construct a base block suitable for a smaller auricle.
Figure 5B:
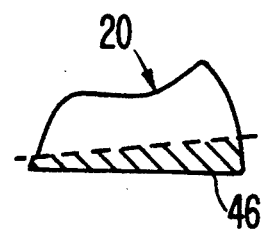
FIG. 5B is a schematic inferior elevation of the base block of FIG. 5A, with shading showing the exemplary portion of the base block which can be removed to construct a smaller auricle.
Figure 5C:
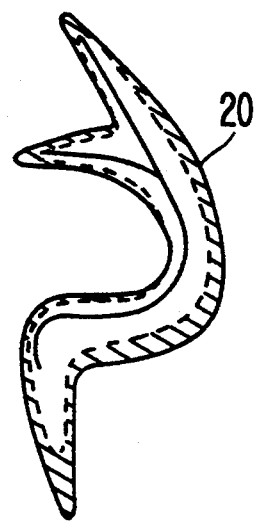
FIG. 5C is a top view of the base block of FIGS. 5A and 5B.
Figure 5D:
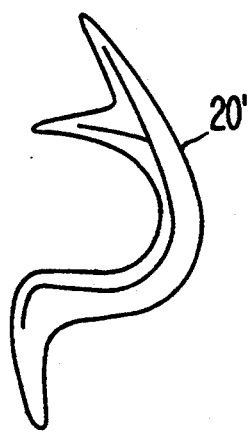
FIG. 5D is a top view of a smaller base block constructed by the removal of the shaded portions of the base blocks of FIGS. 5A–5C.

FIG. 4D illustrates the ability of the helix 10 to deflect and of the implant to fold upon itself when the force F is applied. This property of the implant prevents damage to the implant and injury to the patient.

As can be seen from FIGS. 5A–5D, the base block 20 is formed with a flat base surface 46. The base block 30 tapers over its entire area as it rises above the base surface 46. As a result, removal of portions of the base block by making a cut through the base block which is parallel to or substantially parallel to the base portion 46 results in a new base member 20' having the same general shape as the base member 20, but a smaller height and covering a smaller area. Accordingly, the base block 20 can be adjusted to precisely fit a patient.

Shaping of the components, the helix 10 and the base block 20, is aided by heating them in physiologic saline at its boiling point. At this temperature, they become soft and can be gently molded to their desired shapes while maintaining both the structural integrity and the pore configuration of the material. Upon cooling, the components once again regain their firmer structural characteristics. The remainder of the shaping process is then performed using a scalpel or other sharp cutting instrument. Once completed, the components are soaked in an antibiotic solution containing an appropriate cephalosporin.

The specific tailoring of the components, especially the helix 10, is aided by using models that can be sterilized and utilized on the operating table. Models are made by taking an impression with a dental compound, such as alginate, and pouring a model of dental stone. It is useful to have a model of the site of the deformed ear to establish the way the helix 10 will rest on the auricular remnants. It is also useful to have a model of a normal auricle, either the unaffected contralateral ear or a suitable ear from an uninjured individual.

The first step of the surgical procedure is to position and outline the helical rim on the mastoid skin. In one method by which soft tissue can be provided, a Y-shaped incision is then designed superiorly through which the temporoparietal fascia can be harvested. The temporoparietal fascia (TPF) is harvested in a known manner. The anterior extent of the dissection is carried to 1 cm beyond the superficial temporal vessels. In general, the subgaleal fascia is raised with the superficial temporal fascia. The vascularity of the flap is so robust that it can be raised and utilized effectively even in the face of an occluded superficial temporal artery. In raising the flap, it is important to carry the dissection of the deep surface of the flap distally until the conchal cartilage is reached in order to create an adequate sulcus behind the ear. An incision is made along the superior markings for the helix. A flap of skin or skin graft is raised based on the previous scar until the remaining cartilaginous remnants are feed from enveloping scar tissue. The ends of the helical rim are placed into pockets created in the skin at the normal root of the helix and at the area of the lobule, the entrances to which are represented in FIG. 1A by the dashed lines 38 and 40, respectively. This allows the helical rim 10 to pivot around the central components of the auricle. The projection of the helical rim 10 needs to be greater than what is ultimately desired to compensate for the contraction of the skin graft and rotation of the helix 10 toward the mastoid.

In most cases, suture fixation of the helix 10 has been unnecessary. A small diameter round suction drain is placed along the inside rim of the helix 10. The suction is transmitted through the pores in the framework. The flap is then wrapped around the helical portion of the framework so as to avoid redundant soft tissue that could obscure the detail of the helical rim. It is important to drape the flap to allow for postoperative swelling which will inevitably follow the procedure. The flap is positioned over the framework so that the superficial temporal artery lies over the rim of the helix. The anterior edge of the flap is brought over the helical rim and sutured to the mid-portion of the TPF flap. The posterior edge of the flap is sutured to the posterior aspect of the ear remnants.

A soft flat silicone drain is used in the fascial donor site. Small absorbable sutures are used on the fascia. A useful maneuver is to directly advance the scalp around the ear reconstruction behind the ear into the post auricular sulcus. The skin graft is then applied and should likewise be free of wrinkles, but should be loose enough to allow for the swelling of the underlying TPF fascia. The bolsters for the skin grafts are not sutured, but are secured with a head dressing. Earlobe reconstruction is performed at a later stage.

Secondary operations are performed later, for example, after 6–8 weeks to coincide with other operative procedures commonly required in burn patients. Earlobe reconstruction may be performed in a number of known ways. In the event of wound dehiscence or threatened implant expose, conservative treatment has been applied based on the expectation of rapid vascular ingrowth into the polyethylene framework.

While certain representative embodiments and details have been shown for the purpose of illustrating the invention, it will be apparent to those skilled in this art that various changes and modifications may be made therein without departing from the scope of the invention.

I claim:

1. An auricular implant for reconstructing an auricle having a helical rim, comprising:
   a base member including a body portion;
   a helix member having a helical shape and an inner periphery, the base member being in juxtaposition within the periphery of the helix member to define a framework of the auricle, said framework being adapted to receive a covering of soft tissue, wherein said base member has a bottom and a flat base surface extending entirely across the bottom, and said body portion tapers from said base surface to a peaked upper portion.

2. The auricular implant of claim 1, wherein said base member and said helix member are made of bioimplantable material.

3. The auricular implant of claim 2, wherein said bioimplantable material is porous high-density polyethylene.

4. The auricular implant of claim 1, wherein said base member and said helix member are juxtaposed in any one of a large number of relative positions.

5. The auricular implant of claim 2, wherein said bioimplantable material allows tissue to grow into said bioimplantable material.

6. The auricular implant of claim 2, wherein said bioimplantable material is flexible.

7. The auricular implant of claim 6, wherein at least one portion of said helix member is spaced from said base member, whereby said implant folds upon itself to prevent injury when pressure is applied to the helix member.

8. The auricular implant of claim 1, wherein said helix member has a first side and a second side, said first side being convex in a transverse direction, and said second side being concave in a transverse direction.

9. An auricular implant, comprising:

a strip of material having a length and defining the shape of a helix having a center and a periphery, said strip having a first side facing away from the center of said helix, a second side facing toward the center of said helix, an inner end adjacent to the center of said helix, and an outer end at the periphery of said helix, said first side of said strip being convex in a direction transverse to the length of said strip, and said second side of said strip being concave in a direction transverse to the length of said strip.

10. The auricular implant of claim 9, wherein said material is flexible, porous polyethylene.

11. The auricular implant of claim 9, wherein said first side and said second side are, respectively, convex and concave throughout the length of said strip.

12. The auricular implant of claim 9, further comprising a base member positioned within the helix defined by the strip, whereby an antihelix is provided for the auricular implant.

13. An auricular implant for a human head, comprising:

a strip of material defining the shape of a helix having a center, a periphery, an inner end, and an outer end, said strip of material terminating in a first end coincident with the inner end of the helix and a second end coincident with the outer end of the helix, said material comprising means for attaching said strip to human tissue.

14. The auricular implant of claim 13, wherein said material is flexible, porous polyethylene.

15. The auricular implant of claim 13, wherein said first and second ends of said strip are attached to the head by said attaching means, and said strip is unattached to the head between said first and second ends of the strip.

16. The auricular implant of claim 13, wherein said strip has a length, a first side facing away from the center of the helix, and a second side facing toward the center of the helix;

said first side of said strip is convex in a direction transverse to the length of the strip; and said second side of said strip is concave in a direction transverse to the length of said strip.

17. The auricular implant of claim 13, further comprising a base member positioned within the helix defined by the strip, whereby an antihelix is provided for the auricular implant.

* * * * *

UNITED STATES PATENT AND TRADEMARK OFFICE
CERTIFICATE OF CORRECTION

PATENT NO. : 5,433,748
DATED : July 18, 1995
INVENTOR(S) : Tadeusz Wellisz

It is certified that error appears in the above-indentified patent and that said Letters Patent is hereby corrected as shown below:

Claim 9, column 8, line 1, after "direction", --perpendicularly-- should be inserted;

Claim 13, column 8, line 19, after "for", --instantaneously-- should be inserted;

Claim 15, column 8, line 23, after "said", --means for instantaneously attaching comprises means for attaching said-- should be inserted;

line 24, "are attached" should be deleted;

line 25, "by said attaching means, and" should be deleted;

same line, before "said", --such that-- should be inserted;

Claim 16, column 8, lines 32 and 34, after "direction", --perpendicularly-- should be inserted;

UNITED STATES PATENT AND TRADEMARK OFFICE
CERTIFICATE OF CORRECTION

PATENT NO. : 5,433,748
DATED : July 18, 1995
INVENTOR(S) : Tadeusz Wellisz

It is certified that error appears in the above-indentified patent and that said Letters Patent is hereby corrected as shown below:

Column 8, line 40, the following claim should be inserted:

--18. An auricular implant for a human head, comprising:

a strip of material defining the shape of a helix having a center, a periphery, an inner end, and an outer end, said strip of material terminating in a first end coincident with the inner end of the helix and a second end coincident with the outer end of the helix, said material comprising means for attaching said strip to human tissue in a manner similar to that of a hook-and-loop fastener.--

Signed and Sealed this

Fifteenth Day of October, 1996

*Attest:*

BRUCE LEHMAN

*Attesting Officer*     *Commissioner of Patents and Trademarks*